US009753017B2

United States Patent
Kono et al.

(10) Patent No.: US 9,753,017 B2
(45) Date of Patent: Sep. 5, 2017

(54) ULTRASONIC OBSERVATION EQUIPMENT, ULTRASONIC OBSERVATION SYSTEM, AND ULTRASONIC OBSERVATION METHOD

(71) Applicant: Hitachi-GE Nuclear Energy, Ltd., Hitachi-shi, Ibaraki (JP)

(72) Inventors: Naoyuki Kono, Tokyo (JP); Kouichi Kurosawa, Hitachi (JP); So Kitazawa, Tokyo (JP); Yuji Matsui, Tokyo (JP)

(73) Assignee: Hitachi-GE Nuclear Energy, Ltd., Hitachi-shi (JP)

( * ) Notice: Subject to any disclaimer, the term of this patent is extended or adjusted under 35 U.S.C. 154(b) by 299 days.

(21) Appl. No.: 14/293,421

(22) Filed: Jun. 2, 2014

(65) Prior Publication Data
US 2014/0355378 A1    Dec. 4, 2014

(30) Foreign Application Priority Data

Jun. 3, 2013    (JP) ................. 2013-117211

(51) Int. Cl.
| | |
|---|---|
| *G01S 7/28* | (2006.01) |
| *G01N 29/34* | (2006.01) |
| *G01S 15/89* | (2006.01) |
| *G01N 29/06* | (2006.01) |

(Continued)

(52) U.S. Cl.
CPC ....... *G01N 29/343* (2013.01); *G01N 29/0654* (2013.01); *G01N 29/262* (2013.01);
(Continued)

(58) Field of Classification Search
CPC ........ G01S 7/28; G01S 15/02; G01S 15/8913; G01S 15/8915; G01S 7/003;
(Continued)

(56) References Cited

U.S. PATENT DOCUMENTS

| | | | | |
|---|---|---|---|---|
| 4,409,839 A | * | 10/1983 | Taenzer | G10K 11/26 73/625 |
| 6,126,595 A | * | 10/2000 | Amano | A61B 5/02 600/300 |

(Continued)

FOREIGN PATENT DOCUMENTS

| | | |
|---|---|---|
| JP | 56-71211 | 6/1981 |
| JP | 3-231650 A | 10/1991 |

(Continued)

OTHER PUBLICATIONS

Japanese-Language Office Action issued in counterpart Japanese Application No. 2013-117211 dated Nov. 1, 2016 with English translation (8 pages).

(Continued)

*Primary Examiner* — Luke Ratcliffe
*Assistant Examiner* — Amienatta M N'Dure
(74) *Attorney, Agent, or Firm* — Crowell & Moring LLP

(57) ABSTRACT

A single-element ultrasonic sensor includes a single transducer element and transmits an ultrasonic wave on the basis of a pulse wave. An ultrasonic array sensor includes a plurality of transducer elements and receives an ultrasonic reflected wave. A pulsar supplies the pulse wave to the single element ultrasonic sensor. A receiver receives electric signals from the transducer elements included in the ultrasonic array sensor. An amplification and conversion unit amplifies the electric signals received from the transducer elements included in the ultrasonic array sensor, converts the electric signals into digital signals, and arranges the digital signals in a serial order so as to generate a serial digital signal. An image generator generates an image on the basis of the serial digital signal.

9 Claims, 13 Drawing Sheets

(51) Int. Cl.
*G01N 29/26* (2006.01)
*G21C 17/01* (2006.01)
*G01S 7/00* (2006.01)
*G21C 17/013* (2006.01)

(52) U.S. Cl.
CPC ...... *G01S 15/8913* (2013.01); *G01S 15/8915* (2013.01); *G21C 17/01* (2013.01); *G01N 2291/106* (2013.01); *G01N 2291/2636* (2013.01); *G01S 7/003* (2013.01); *G21C 17/013* (2013.01)

(58) Field of Classification Search
CPC ............. G01N 29/0654; G01N 29/262; G01N 29/343; G01N 2291/106; G01N 2291/2636; G21C 17/01; G21C 17/013
USPC .......................................................... 367/11
See application file for complete search history.

(56) References Cited

U.S. PATENT DOCUMENTS

| | | | |
|---|---|---|---|
| 7,892,175 B2* | 2/2011 | Wakabayashi | A61B 8/12 600/437 |
| 2003/0100832 A1 | 5/2003 | Criton et al. | |
| 2007/0167814 A1* | 7/2007 | Wakabayashi | A61B 8/12 600/459 |
| 2007/0187632 A1* | 8/2007 | Igarashi | A61B 5/0048 250/559.36 |
| 2009/0003506 A1* | 1/2009 | Kitazono | G21C 17/108 376/259 |
| 2009/0221900 A1* | 9/2009 | Ikushima | A61B 5/0093 600/409 |

FOREIGN PATENT DOCUMENTS

| | | |
|---|---|---|
| JP | 10-26614 A | 1/1998 |
| JP | 11-14784 A | 1/1999 |
| JP | 11-234797 A | 8/1999 |
| JP | 2003-164453 A | 6/2003 |
| JP | 2005-127870 A | 5/2005 |
| JP | 2006-284417 A | 10/2006 |
| JP | 2010-227356 A | 10/2010 |

OTHER PUBLICATIONS

Japanese-language Office Action issued in counterpart Japanese Application No. 2013-117211 dated May 23, 2017 (Four (4) pages).

* cited by examiner (FIRST COMPARATIVE EXAMPLE)

(FIRST COMPARATIVE EXAMPLE)

(SECOND COMPARATIVE EXAMPLE)

ULTRASONIC OBSERVATION EQUIPMENT, ULTRASONIC OBSERVATION SYSTEM, AND ULTRASONIC OBSERVATION METHOD

BACKGROUND OF THE INVENTION

1. Field of the Invention

The present invention relates to an observation method and equipment that use an ultrasonic reflected wave within a liquid or a solid.

2. Description of the Related Art

An ultrasonic observation technique is used for inspection of a structure or the like in water and non-destructive inspection of the inside of a solid (steel material or the like). It is one of techniques for transmitting an ultrasonic wave to an object to be observed and visualizing a change in a physical amount of the object based on a wave reflected from the object to be observed.

For example, inspecting objects to be observed in water (such as a river and an ocean) involves attachment of observation equipment for inspection to a ship or a remotely-operated vehicle. In non-destructive testing, an operator may physically hold the observation equipment or attach it to an automated scanner to perform the inspection.

In both cases above, means, which could be an operator or an automated device such as a remotely-operated vehicle or an automated scanner, for transporting the observation equipment to an object to be observed is required. If the object to be observed is small but the volume of the observation equipment is large, an observation operation may be limited.

That case then needs the observation equipment to be downsized. As one of downsized equipment an ultrasonic inspection device, which is downsized as much as possible and is high-sensitive, is known (refer to, for example, JP-2005-127870-A).

SUMMARY OF THE INVENTION

As disclosed in JP-2005-127870-A, two methods are available for a case in which a phased array ultrasonic inspection device is used to remotely observe a cramped portion. The first method is to cause only an array transducer to approach a place located near the portion to be observed. In this method, a multicore coaxial cable that connects the array transducer to a transceiver is required to be longer.

In order to suppress signal attenuation due to the length of the cable, a large-diameter and heavy multicore coaxial cable needs to be used. This case will increase a load to be applied to the means, the operator or scanner, for transporting observation equipment.

On the contrary, taking precedence in a reduction in the weight of the cable will necessitate the cable to be thinner. The thinner cable will make the signal attenuation greater, which will impede the ensuring an excellent signal-to-noise ratio (SN ratio) in receiving wave of an ultrasonic wave.

The second method is to cause the array transducer and the transceiver to approach a place near the object to be observed. In order to cause the transceiver to approach the cramped portion to be observed, the transceiver needs to be downsized. In general, the transceiver requires an electric circuit for transmitting and receiving a signal and an electric circuit for executing a complex process such as delay control, and therefore, the downsizing of the transceiver is limited. In addition, a tradeoff, which leads to a reduction in the resolution of an ultrasonic image, could occur instead of the downsizing although the transceiver can be smaller by reducing the number of transducer elements in the array transducer that can be used for the circuit.

It has traditionally been difficult to use an ultrasonic wave to visualize an object to be observed located at a cramped portion while maintaining the quality of an ultrasonic image.

An object of the invention is to provide ultrasonic observation equipment, an ultrasonic observation system, and an ultrasonic observation method that enable an object that is to be observed located at a cramped portion to be visualized using an ultrasonic wave while maintaining the quality of an ultrasonic image.

In order to accomplish the aforementioned object, ultrasonic observation equipment includes a pulsar configured to generate a pulse wave, a single element ultrasonic sensor for transmitting including a single transducer element and configured to transmit an ultrasonic wave on the basis of the pulse wave, an ultrasonic array sensor for receiving including a plurality of transducer elements and configured to receive an ultrasonic reflected wave, a receiver configured to receive electric signals from the transducer elements included in the ultrasonic array sensor, an amplification and conversion unit configured to amplify the electric signals received by the receiver from the transducer elements included in the ultrasonic array sensor, convert the electric signals into digital signals, and arrange the digital signals in a serial order so as to generate a serial digital signal, and an image generator configured to generate an image on the basis of the serial digital signal.

According to the invention, an object to be observed located at a cramped portion can be easily visualized with the use of an ultrasonic wave while the quality of an ultrasonic image is maintained. Objects, configurations, and effects other than those described above are clarified through a description of the following embodiments.

DESCRIPTION OF THE PREFERRED EMBODIMENTS

First Embodiment

Hereinafter, a configuration and operations of an ultrasonic observation system 100 that includes ultrasonic observation equipment 10 according to a first embodiment of the invention are described with reference to FIGS. 1 to 7. In the first embodiment, the ultrasonic observation equipment 10 uses an ultrasonic wave to observe a pipe included in a nuclear reactor as an example. For inspection of the inside of the reactor of a nuclear power plant, a structure to be inspected and included in the reactor is under water as an example.

Figure 1:
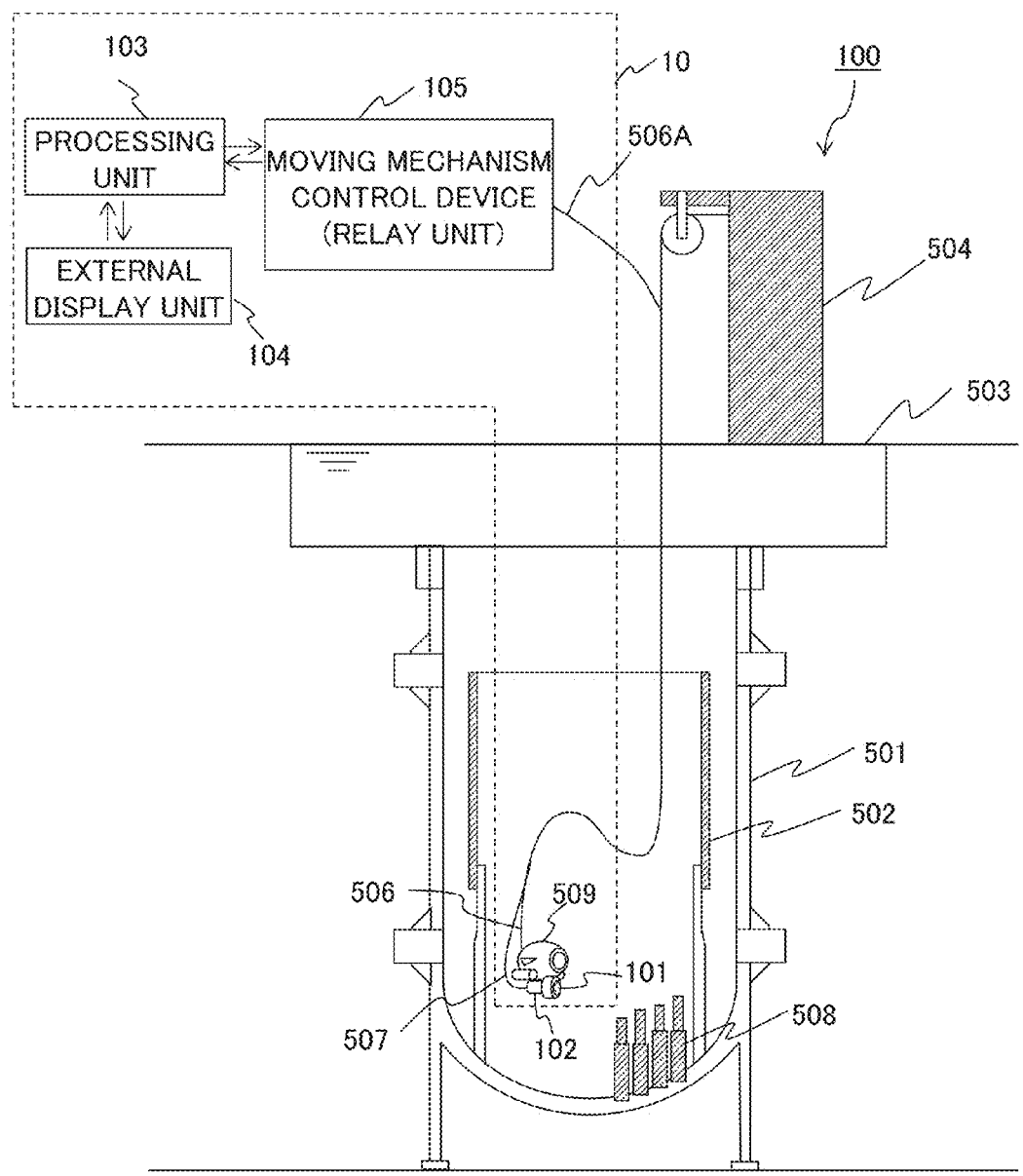
FIG. 1 is a diagram illustrating a configuration of an ultrasonic wave observation system that includes ultrasonic observation equipment according to a first embodiment of the invention.

First, an overall configuration of the ultrasonic observation system 100 that includes the ultrasonic observation equipment 10 according to the first embodiment of the invention will be described with reference to FIG. 1. FIG. 1 is a diagram illustrating the configuration of the ultrasonic observation system 100 that includes the ultrasonic observation equipment 10 according to the first embodiment of the invention. Hereinafter, the same parts are denoted by the same reference numerals.

The ultrasonic observation system 100 is mainly constituted of the ultrasonic observation equipment 10. The ultrasonic observation equipment 10 includes an ultrasonic sensor 101, a small ultrasonic transceiver 102, a processing unit 103, a display unit 104, and a traveling mechanism control device 105 (or a relay unit 105). Details of a configuration of the ultrasonic observation equipment 10 will be described later with reference to FIG. 3.

The nuclear reactor includes a reactor pressure vessel 501, a shroud 502, and an incore structure 508 as objects to be observed by the ultrasonic observation equipment 10. Representative examples of the incore structure are a control rod driving housing (CRDH) stub tube extending through a bottom portion of the reactor pressure vessel 501, a stub tube for control rod driving system, an incore monitoring housing (ICMH) tube, and a shroud support.

For example, the CRDH and the ICMH are each composed of approximately 100 tubes or more placed close to each other in the reactor pressure vessel with a radius of approximately 7 meters. Thus, the objects to be observed are located in a cramped space (or at a cramped portion).

The ultrasonic sensor 101 and the small ultrasonic transceiver 102 are mounted on the underwater traveling mechanism 509. The processing unit 103, the display unit 104, and the traveling mechanism control device 105 are arranged on an operating floor 503 placed in an air environment.

An operation carriage 504 is used to suspend the underwater traveling mechanism 509 by use of a composite cable 506A under water in the reactor, the underwater traveling mechanism 509 having the ultrasonic sensor 101 and the small ultrasonic transceiver 102 mounted thereon. The composite cable 506A is configured to include a cable 506 to be used to control the traveling mechanism, a cable 507 for the ultrasonic observation equipment, and a high-strength resin string, for example.

The composite cable 506A is configured to include the cable 506 and the cable 507 that have different cable cores, for example. The cables 506 and 507 that are constituent elements of the composite cable 506A may use the same optical fiber through which a signal is transferred in serial form.

Figure 2:
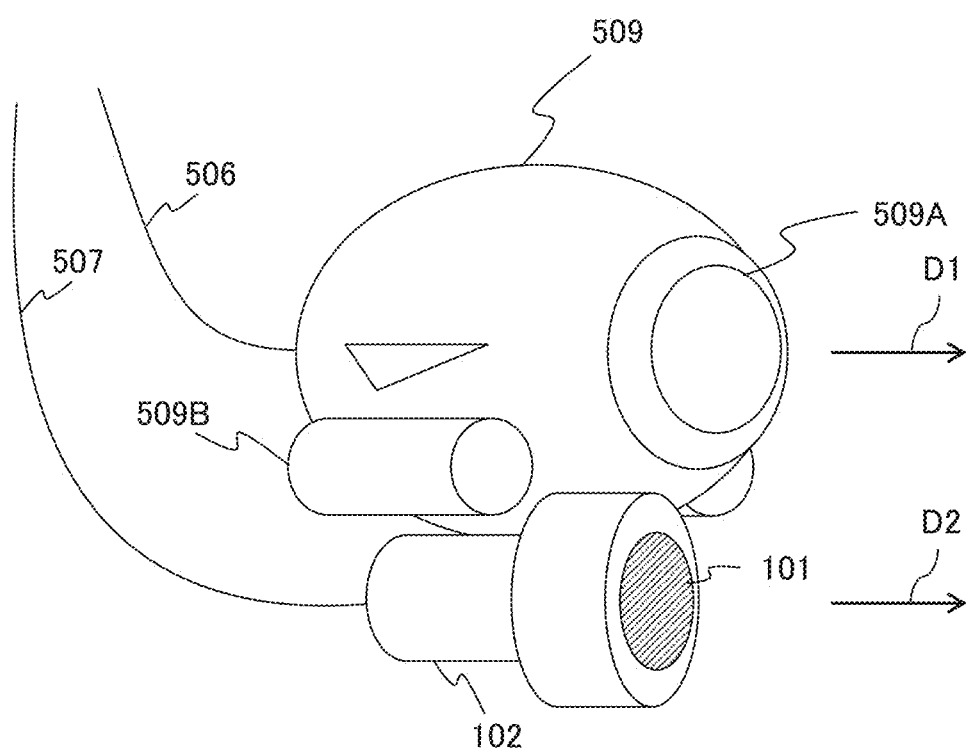
FIG. 2 is an enlarged view of an underwater traveling mechanism included in the ultrasonic observation equipment according to the first embodiment of the invention.

A configuration of the underwater traveling mechanism 509 included in the ultrasonic observation equipment 10 according to the first embodiment of the invention will now be described with reference to FIG. 2. FIG. 2 is an enlarged view of the underwater traveling mechanism 509 included in the ultrasonic observation equipment 10 according to the first embodiment of the invention.

The underwater traveling mechanism 509 includes the ultrasonic sensor 101, the small ultrasonic transceiver 102, an optical camera 509A, and an underwater movement promoting mechanism 509B.

As illustrated in FIG. 2, the ultrasonic sensor 101 is provided with the underwater traveling mechanism 509 in such a manner as to observe an object with an ultrasonic wave in a direction D2 (for example, a front side of the underwater traveling mechanism 509) parallel to a direction D1 in which the optical camera 509A of the underwater traveling mechanism 509 observes an object.

The ultrasonic sensor 101 and the small ultrasonic transceiver 102 are integrated with each other, for example, in order to downsize the equipment. The small ultrasonic transceiver 102 is connected to the traveling mechanism control device 105.

The traveling mechanism control device 105 buffers received digital data in a storage unit of the traveling mechanism control device 105. A communication unit 105A of traveling mechanism control device 105 communicates with the processing unit 103. A personal computer may be used instead of the traveling mechanism control device 105.

Figure 3:
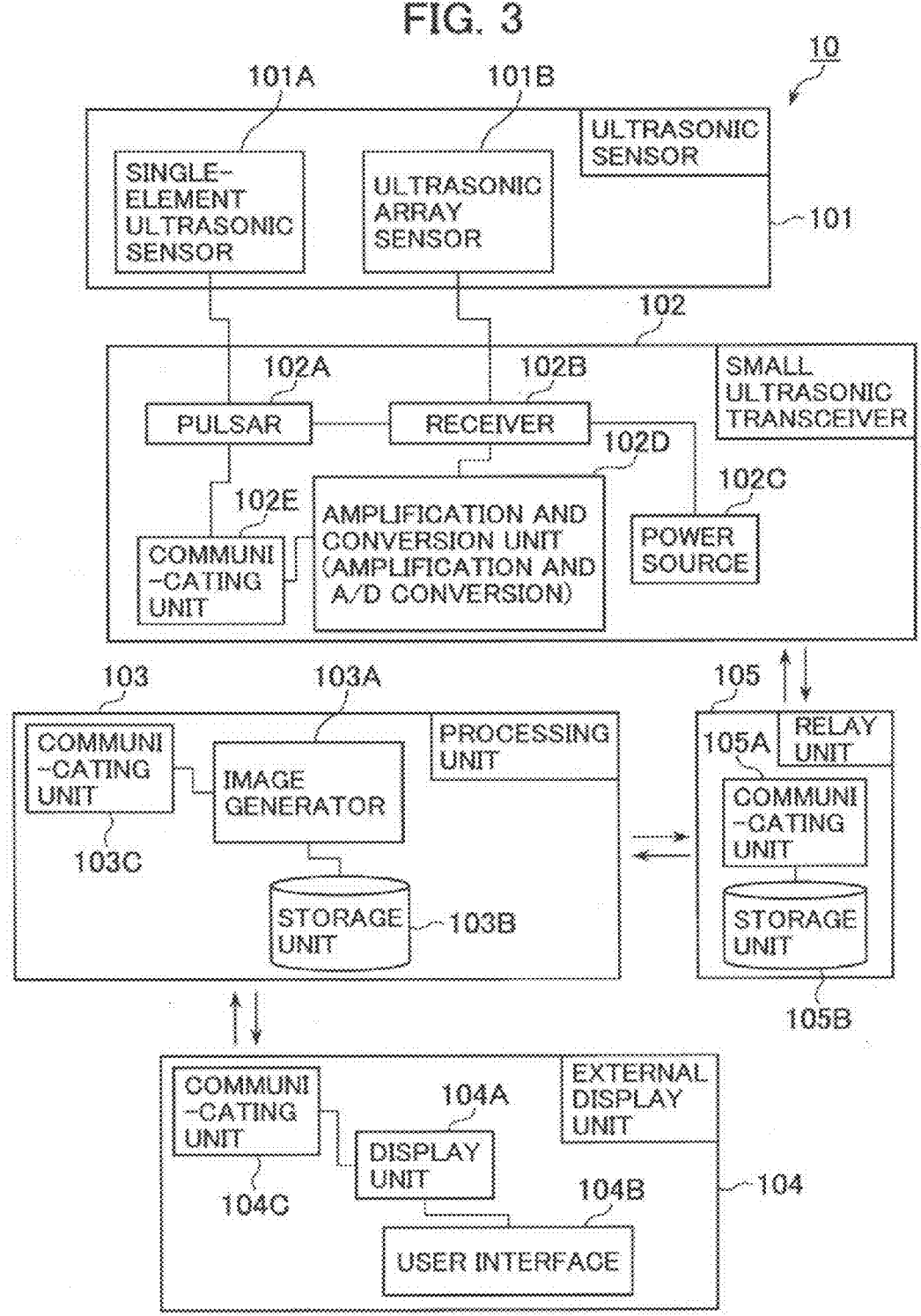
FIG. 3 is a block diagram illustrating the ultrasonic observation equipment according to the first embodiment of the invention.

A configuration of the ultrasonic observation equipment 10 according to the first embodiment of the invention will now be described with reference to FIG. 3. FIG. 3 is a block diagram illustrating the ultrasonic observation equipment 10 according to the first embodiment of the invention.

The ultrasonic observation equipment 10 includes the ultrasonic sensor 101, the small ultrasonic transceiver 102, the processing unit 103, the display unit 104, and the traveling mechanism control device 105 serving as the relay unit. The traveling mechanism control device 105 may not be installed, and the small ultrasonic transceiver 102 and the processing unit 103 may communicate directly with each other.

The ultrasonic sensor 101 for transmission and reception includes a single element ultrasonic sensor for transmitting 101A and an ultrasonic array sensor for receiving 101B. The single element ultrasonic sensor for transmitting 101A includes a single transducer element. The ultrasonic sensor 101B includes a group of minute transducer elements regularly arranged in an array.

The single transducer element of the single element ultrasonic sensor for transmitting 101A generates a single ultrasonic wave in accordance with a voltage applied. The single element ultrasonic sensor for transmitting 101A, however, may have a plurality of transducer elements connected in parallel to each other, and the same voltage may be applied to the single element ultrasonic sensor for transmitting 101A.

The single element ultrasonic sensor for transmitting 101A is displaced and generates an ultrasonic wave on the basis of a high-voltage electric signal (a high-voltage pulse wave of 100V, for example) transmitted from a pulsar 102A. In addition, the ultrasonic array sensor for receiving 101B converts displacements caused due to received weak ultrasonic waves into electric signals and transmits the electric signals to a receiver 102B.

The small ultrasonic receiver 102 includes the pulsar 102A, the receiver 102B, an amplification and conversion unit 102D, a power source 102C, and a communication unit 102E.

The pulsar 102A is connected to the single element ultrasonic sensor for transmitting 101A. The receiver 102B is connected to the ultrasonic array sensor for receiving 101B. The amplification and conversion unit 102D amplifies received electric signals and executes analog-to-digital conversion so as to convert the amplified electric signals into digital signals.

The communication unit 102E transfers a trigger signal (such as rectangular pulse wave) to be used to control the timing of the generation of the high-voltage pulse wave to be supplied from the pulsar 102A for the generation of an ultrasonic wave and transfers the digital signals converted from the received wave by the amplification and conversion unit 102. The power source 102C supplies power to these constituent elements 102A, 102B, 102D, and 102E.

The processing unit 103 includes an image generator 103A, a storage unit 103B, and a communication unit 103C. The image generator 103A generates an ultrasonic image from the digital signals of the received wave. The image generator 103A causes the generated ultrasonic image to be stored in the storage unit 103B.

The communication unit 103C communicates with the communication unit 102E of the small ultrasonic transceiver 102 through the relay unit 105. The communication unit 103C transmits the ultrasonic image generated by the image generator 103A to the external display unit 104.

The external display unit 104 includes a display unit 104A, a user interface 104B (input unit), and a communication unit 104C. The external display unit 104 displays image data of the received wave on the display unit 104A. A user uses the user interface 104B (input unit) to operate the ultrasonic observation equipment 10.

The communication unit 104C receives the image data transmitted from the communication unit 103C of the processing unit 103. The communication unit 104C transfers a control command (such as an instruction to transmit an ultrasonic wave and an instruction to record the received wave) input through the user interface 104B operated by the user.

The control command (control signal) is input from the user interface 104B of the external display unit 104 and transferred through the processing unit 103 and the relay unit 105 to the small ultrasonic transceiver 102. The communication at this time is executed wirelessly or through cables by the communication units (102E, 105A, 103C, and 104C).

The processing unit 103 may communicate with the external display unit 104 through the relay unit 105.

The relay unit 105 includes a communication unit 105A and a storage unit 105B. The relay unit 105 causes received digital data to be buffered in the storage unit 105B and communicates with the processing unit 103 and other units through the communication unit 105A.

A wireless relay unit provided with a function such as a hub or other control devices to be used with the ultrasonic observation equipment may be used as the relay unit 105. Communication between the relay unit 105 and the small ultrasonic transceiver 102, and communication between the relay unit 105 and the processing unit 103 are each wireless or by way of a cable.

Figure 4:
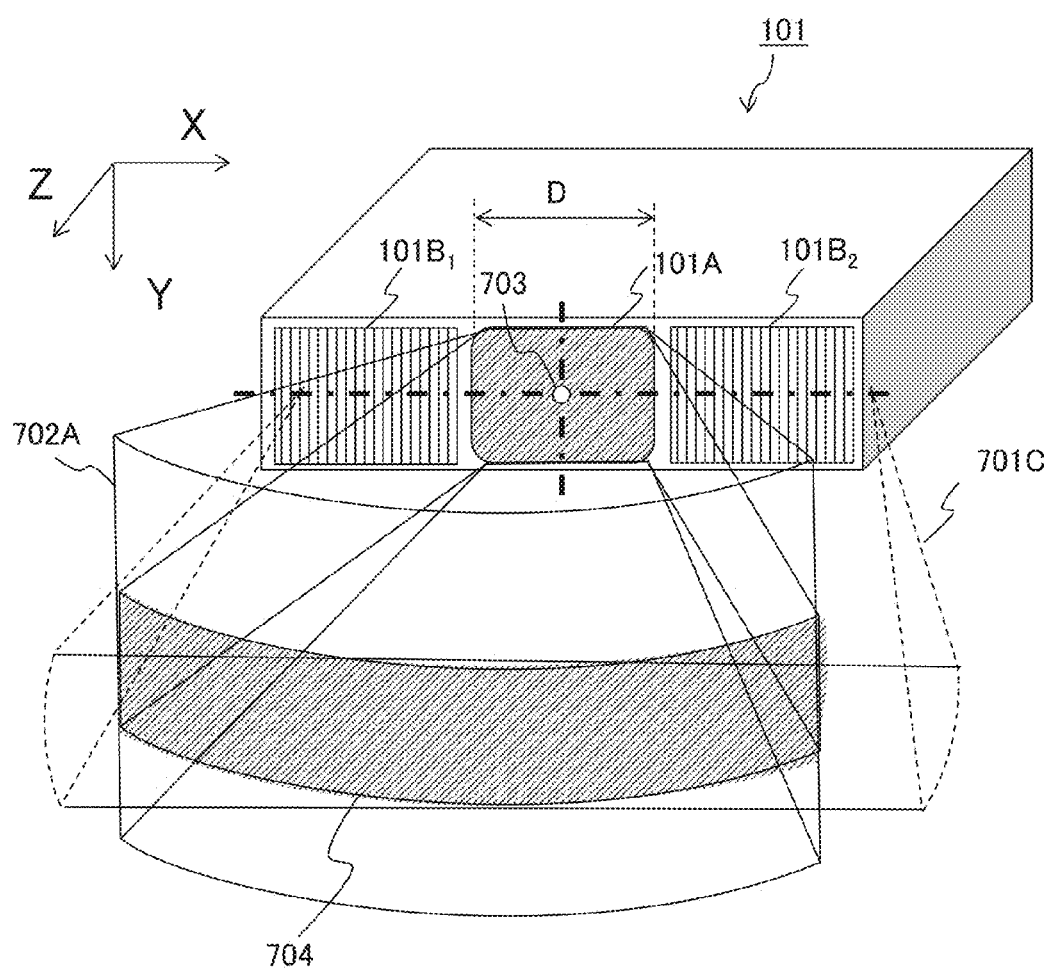
FIG. 4 is a diagram illustrating a configuration of an ultrasonic sensor included in the ultrasonic observation equipment according to the first embodiment of the invention.

A configuration of the ultrasonic sensor 101 included in the ultrasonic observation equipment 10 according to the first embodiment of the invention will now be described with reference to FIG. 4. FIG. 4 is a diagram illustrating the configuration of the ultrasonic sensor 101 included in the ultrasonic observation equipment according to the first embodiment of the invention.

The ultrasonic sensor 101 for transmission and reception includes the single element ultrasonic sensor for transmitting 101A and a receiving array sensor divided into two sensors $101B_1$ and $101B_2$. The receiving array sensors $101B_1$ and $101B_2$ each have a transducer element group. In FIG. 4, an X axis represents a direction in which the transducer elements that form the receiving array sensors are arranged, a Y axis represents a direction perpendicular to the X axis in a plane in which the transducer elements are arranged, and a Z axis represents a normal of the elements (for transmission and reception). It is assumed that the directions of the coordinate axes are defined in the same manner in FIG. 4 and later.

An acoustic field 702A of an ultrasonic wave transmitted is formed to be spread from the single element ultrasonic sensor for transmitting 101A. In order to spread the acoustic field, there are a method for spreading a beam in a directivity angular range θ (θ∝λ/D, where λ is a wavelength of the ultrasonic wave) from the elements with a dimension D reduced, a method for diffusing an acoustic field with the use of an acoustic lens, and other methods.

In the example illustrated in FIG. 4, the dimension D in the X axis direction is reduced, and a spreading angle of the beam is increased. However, a dimension of the elements in the Y axis direction may be reduced, while the spreading angle of the beam is increased.

An acoustic field 701C of a wave to be received by the ultrasonic array sensor for receiving 101B (including the receiving array sensors $101B_1$ and $101B_2$) is formed so as to spread in the direction (X axis direction) in which the elements of the array are arranged. A range in which the ultrasonic wave can be imaged is a region 704 in which the acoustic field 702A of the ultrasonic wave transmitted overlaps the acoustic field 701C of the ultrasonic wave to be received.

Accordingly, the region 704 in which the acoustic fields 702A and 701C intersects with each other only needs to be widened in order to increase the range in which the ultrasonic wave can be imaged. For example, the single element ultrasonic sensor for transmitting 101A and the ultrasonic array sensor for receiving 101B (including the receiving array sensors $101B_1$ and $101B_2$) are arranged in such a manner that the position 703 of the center of the single element ultrasonic sensor for transmitting 101A matches the position 703 of the center of the ultrasonic array sensor for receiving 101B (including the receiving array sensors $101B_1$ and $101B_2$).

First Comparative Example

Figure 5A:
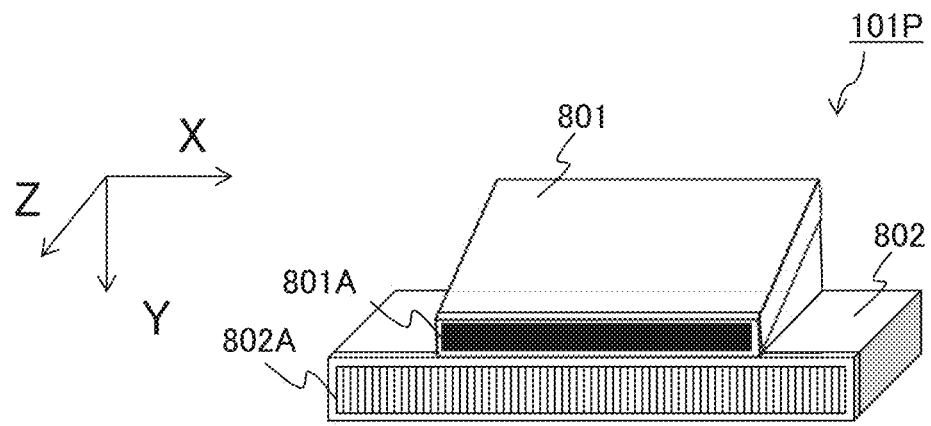
FIG. 5A is a perspective view of an ultrasonic sensor according to a first comparative example.
Figure 5B:
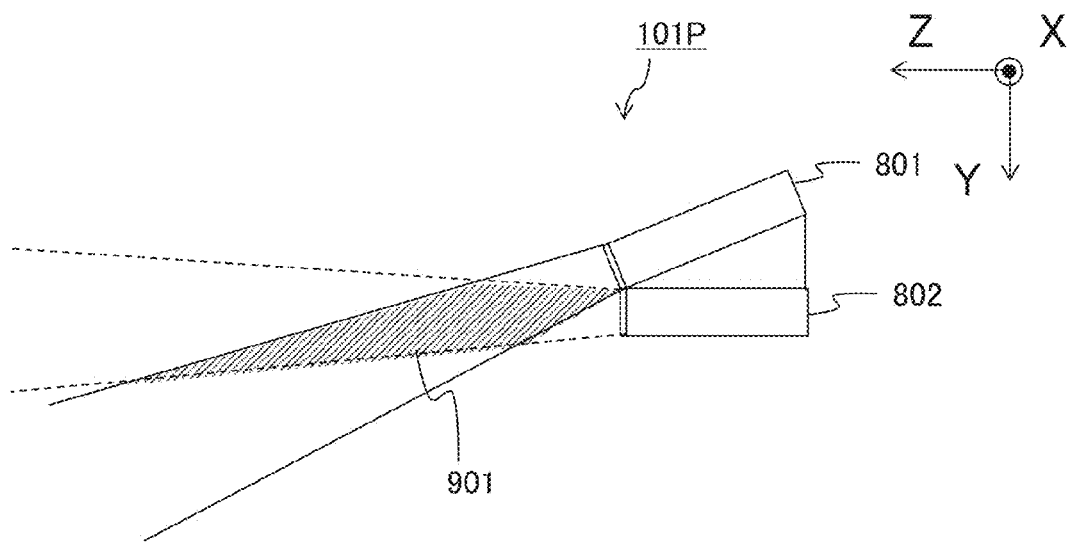
FIG. 5B is a side view of the ultrasonic sensor according to the first comparative example.

A configuration of an ultrasonic sensor 101P according to a first comparative example will now be described with reference to FIGS. 5A and 5B. FIG. 5A is a perspective view of the ultrasonic sensor 101P according to the first comparative example. FIG. 5B is a side view of the ultrasonic sensor 101P according to the first comparative example.

As illustrated in FIG. 5A, the ultrasonic sensor 101P for transmission and reception has a transmitting sensor 801 and a receiving sensor 802 that are arranged side by side in the vertical direction (Y axis direction).

As illustrated in FIG. 5B, the transmitting sensor 801 is located to be slightly rotated around the X axis with respect to the receiving array sensor 802. An acoustic field formed by an element 801A of the transmitting sensor 801 and an acoustic field formed by a group 802A of elements of the receiving array sensor 802 intersect with each other in an acoustic field intersection region 901 as illustrated in FIG. 5B. The intersected region can be imaged.

As illustrated in FIG. 5A, if the positions of the centers of the transmitting and receiving sensors 801 and 802 are shifted from each other, a range in which a wave can be imaged is limited to the intersection region 901 in the Z axis direction, and the shift prevents a wave from being imaged in a large range.

Figure 6:
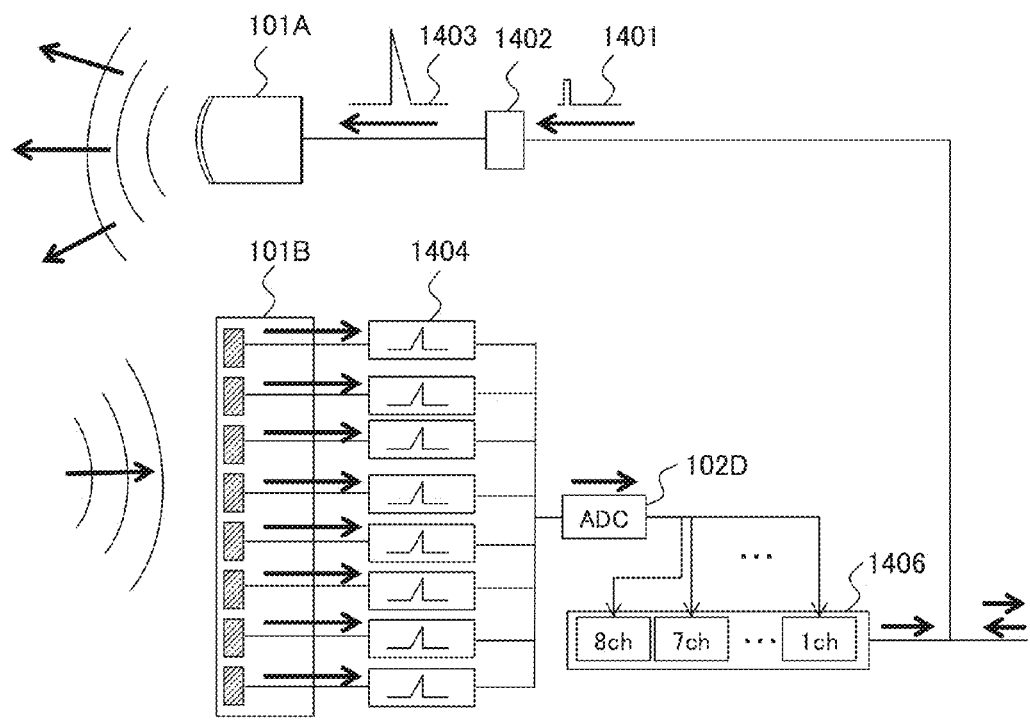
FIG. 6 is a diagram describing an example of parts included in constituent elements of the ultrasonic observation equipment according to the first embodiment of the invention and involved in transmission and reception of an ultrasonic wave.

Operations of the ultrasonic observation equipment 10 according to the first embodiment of the invention are described with reference to FIG. 6, which is a diagram describing an example of parts included in the constituent elements of the ultrasonic observation equipment 10 according to the first embodiment of the invention and involved in transmission and reception of an ultrasonic wave. FIG. 6 is the schematic diagram illustrating that the single element ultrasonic sensor for transmitting 101A and the ultrasonic array sensor for receiving 101B are separated in order to describe the example. The single element ultrasonic sensor for transmitting 101A and the ultrasonic array sensor for receiving 101B, however, are actually integrated with each other as illustrated in FIG. 4.

When an instruction to control ultrasonic transmission is provided through the user interface 104 of the external display unit 104 in accordance with an operation of the user, the communication unit 104C transmits a control signal through the processing unit 103 to the ultrasonic transceiver 102.

The control signal that serves as a trigger signal 1401 (or a transmission trigger) is input to a high-voltage generator 1402 included in the pulsar 102A of the small ultrasonic transceiver 102. The high-voltage generator 1402 is synchronized with the trigger signal and generates a high-voltage pulse 1403. The high-voltage pulse 1403 is transmitted to the single element ultrasonic sensor for transmitting 101A.

The single element ultrasonic sensor for transmitting 101A is displaced and generates an ultrasonic wave on the basis of the high-voltage pulse 1403 transmitted from the pulsar 102A. The single element ultrasonic sensor for transmitting 101A transmits the ultrasonic wave that spreads toward an object to be observed.

The ultrasonic array sensor for receiving 101B converts displacements caused due to an ultrasonic wave reflected on the object to be observed into electric signals 1404. Specifically, the transducer elements (channels) that form the ultrasonic array sensor for receiving 101B generate the electric signals 1404 on the basis of the respective displacements. As a result, one electric signal 1404 corresponds to one channel.

The amplification and conversion unit 102D that supports the multiple channels converts the received signals (electric signals) of each channel into digital signals per channel. The amplification and conversion unit 102D arranges the digital signals for the channels in a serial order or in the order of the arrangement of the channels and transmits the digital signals as a serial digital signal 1406 to the processing unit 103.

Figure 7:
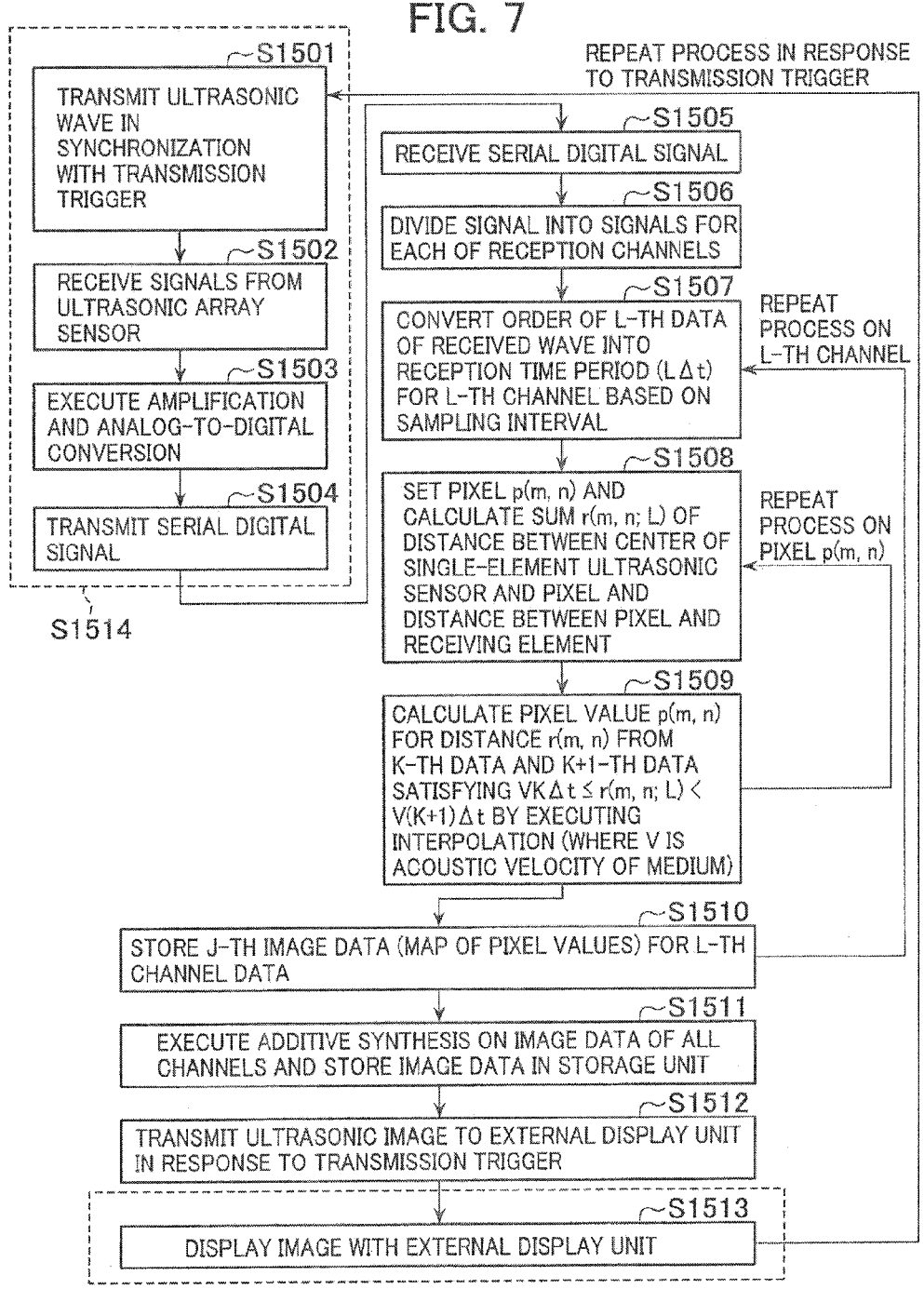
FIG. 7 is a flowchart of operations of the ultrasonic observation equipment according to the first embodiment of the invention.

Operations of the ultrasonic observation equipment 10 according to the first embodiment of the invention will now be described with reference to FIG. 7. FIG. 7 is a flowchart of the operations of the ultrasonic observation equipment 10 according to the first embodiment of the invention. The flowchart is mainly constituted of a process of transmitting an ultrasonic wave, a process of receiving an ultrasonic wave, and a process of imaging the ultrasonic wave received.

When an instruction to control the ultrasonic transmission is provided through the user interface 104B of the external display unit 104 in accordance with an operation of the user, the communication unit 104C transmits a control signal through the processing unit 103 to the ultrasonic transceiver 102.

The control signal that serves as the trigger signal 1401 (or the transmission trigger) is input to the high-voltage generator 1402 included in the pulsar 102A of the ultrasonic transceiver 102.

The single element ultrasonic sensor for transmitting 101A is synchronized with the trigger signal and transmits an ultrasonic wave that spreads toward the object to be observed (in step S1501). The ultrasonic array sensor for receiving 101B converts a wave reflected from the object to be observed into electric signals and transmits the electric signals to the receiver 102B.

The receiver 102B receives, from the ultrasonic array sensor for receiving 101B, the electric signals of the wave reflected from the object to be observed (in step S1502). The receiver 102B supplies the analog electric signals received from the ultrasonic array sensor for receiving 101B and converted from the reflected wave to the amplification and conversion unit 102D. The amplification and conversion unit 102D amplifies and converts the received analog electric signals into digital signals per transducer element (channel) included in the ultrasonic array sensor for receiving 101B (in step S1503). The amplification and conversion unit 102D arranges the digital signals for each channel in a serial order and transmits the digital signals as a serial digital signal 1406 to the processing unit 103 (in step S1504).

A group S1514 of steps S1501 to S1504 is mainly executed at the ultrasonic transceiver 102.

The communication unit 103C of the processing unit 103 (image processing unit) receives the serial digital signal 1406 from the amplification and conversion unit 102D (in step S1505). The image generator 103A divides the received serial digital signal into signals for each of the channels (in step S1506).

The image generator 103A converts, for a J-th channel (J-th transducer element of the receiving array sensor), the L-th data order (L) of the received signal is converted into a reception time period LΔt corresponding to a round-trip propagation time on the basis of an acoustic velocity V of a medium located near the object to be observed and a sampling interval (Δt) (in step S1507).

Thus, a digital data point sequence has strength of I (L) and can be regarded as a digital data point sequence having strength I (LΔt) for the reception time period LΔt due to the conversion.

An ultrasonic image is formed as a map of digital data with pixel values of pixels two-dimensionally arranged in general. It is assumed that the number of all the pixels is M×N and a value of a pixel located at two dimensional coordinates (m, m) within the ultrasonic image is represented by p(m, n). For example, in order to generate a certain image, it is necessary to sequentially determine a pixel value for each of the number M×N of the pixels.

A method for sequentially calculating the pixel values p(m, n) is described below while m is in a range of 1 to M, and n is in a range of 1 to N. The image generator 103A calculates, for the position (m, n) of a certain pixel, a sum r (m, n; L) of a distance between the center of the transmitting sensor and the pixel (m, n) and a distance between the pixel (m, n) and a receiving element (channel) with respect to data of the L-th channel (in step S1508).

The image generator 103A calculates a pixel value p(m, n) of the pixel (m, n) by use of interpolating strength I(KΔt) and I[(K+1)Δt], calculated according to Inequality (1), of K-th digital data into the following Equation (2) (in step S1509). The interpolation is not limited to linear correlation of Equation (2) and may be correlation with the use of a polynomial.

Inequality (1)

$$VK\Delta t \leq r(m,n) < V(K+1)\Delta t \quad (1)$$

Equation (2)

$$p(m,n) = b/(a+b)*I[(K)\Delta t] + a/(a+b)*I[(K+1)\Delta t] \quad (2),$$

where a=r(m, n)−VKΔt, b=V(K+1)Δt−r(m, n), and a+b=VΔt.

The image generator 103A repeatedly calculates the positions (m, n) of the pixels and thereby generates a map of values of the number M×N of all the pixels so as to generate an image. The image is for the L-th channel. The image generator 103A causes the image to be stored in the storage unit (in step S1510).

Whichever pixel positions the calculation of a pixel value is started from, the calculation of the pixel value of the pixel position (m, n) will not affect pixel values of the other pixel positions in principle. Since an algorithm that enables arithmetic elements of the image generator 103A to easily calculate pixel values in parallel is used, speeding up the imaging processing can be achieved.

The image generator 103A can generate images for all the channels included in the ultrasonic array sensor through repeating the process that is executed on the L-th channel.

The image generator 103A sums images for the pixel positions (m, n) according to the following Equation (3) and thereby calculates pixel values p(m, n) of a received image. In Equation (3), Σ_L represents an addition of the values to the channel L.

$$p(m,n) = \Sigma\_L p(m,n;L) \quad (3)$$

Image computation related to a reception channel can be executed independently from image computation related to another channel. Accordingly, image construction of each channel can be easily calculated in parallel, whereby the speeding-up of image processing is achieved.

The image generator 103A causes image data obtained as a result of summing the images according to Equation (3) to be stored in the storage unit 103B (in step S1511). An image obtained as a result of summing images from all the channels is an ultrasonic image of the received signal. The image generator 103A transmits the ultrasonic image formed in response to the transmission trigger used in S1501 to the external display unit 104 (in step S1512). The external display unit 104 displays data of the ultrasonic image transmitted from the processing unit 103 on the display unit 104A (in step S1513).

If a certain repetition frequency is set up after the display of the ultrasonic image, the image generator 103A generates a transmission trigger for ultrasonic transmission and transmits the transmission trigger to the small ultrasonic receiver 102. As a result, a command to transmit an ultrasonic wave is transmitted to the small ultrasonic receiver 102.

A group of steps S1505 to S1512 is executed at the processing unit 103.

As described above, in the present embodiment, the small ultrasonic receiver 102 performs neither a complex delay control nor a complex synthesis process. Instead, the small ultrasonic receiver 102 transmits the serial digital signal obtained as a result of conversion of the received wave to the processing unit 103, thereby making it possible to downsize the ultrasonic transceiver. Since it is not necessary to reduce the number of transducer elements, the quality of an ultrasonic image can be maintained.

In addition, the single element ultrasonic sensor for transmitting 101A that includes the single transducer element transmits an ultrasonic wave, whereby a circuit for transmission can be simplified and the equipment can be downsized.

Downsizing of the transceiver makes visualization of an object to be observed located at a cramped portion easier with the use of an ultrasonic wave.

Further, the processing unit 103 processes a digital signal using the algorithm that enables the parallel process to be easily executed. Thus, the processing unit 103 that has high throughput can be placed far from the transceiver 102, as well as execute the image processing at a high speed. In this case, an ultrasonic image is transferred to the external display unit 104 through communication, whereby the user can confirm the image displayed rapidly.

First Modified Example

Figure 8:
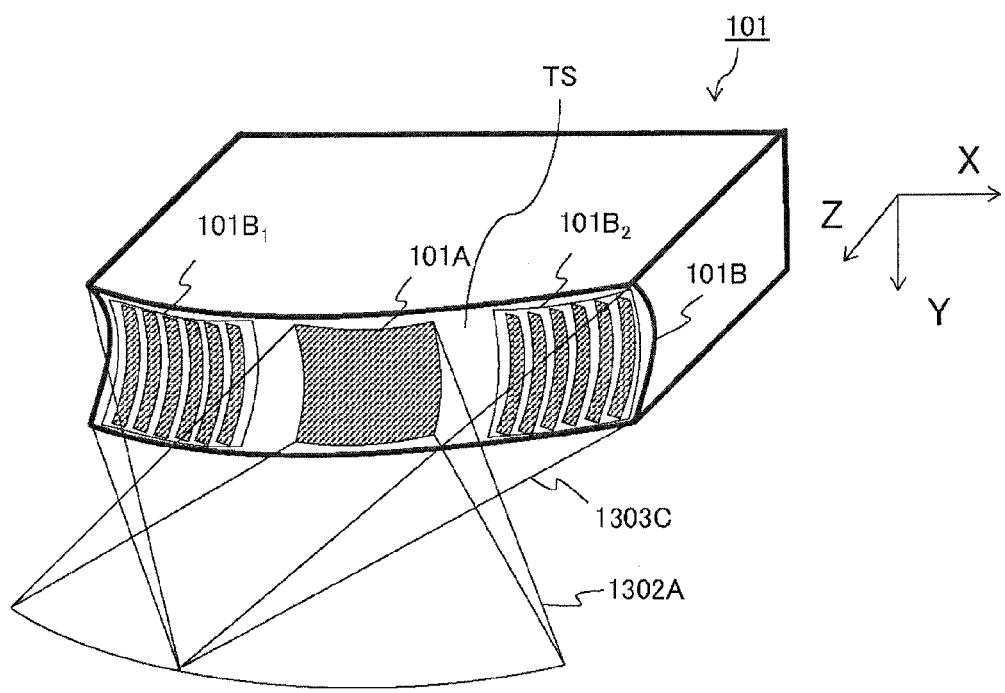
FIG. 8 is a diagram illustrating a configuration of an ultrasonic sensor according to a first modified example.

A configuration of the ultrasonic sensor 101 according to a first modified example will now be described with reference to FIG. 8. FIG. 8 is a diagram illustrating the configuration of the ultrasonic sensor 101 according to the first modified example.

Since the ultrasonic sensor 101 does not need to contact an object to be observed in underwater inspection, a front surface of the ultrasonic sensor 101 may have curvature.

The ultrasonic sensor 101 has protruding surface portions extending in the direction (X axis direction) parallel to the direction in which the transducer element groups (101B$_1$ and 101B$_2$) that form the ultrasonic array sensor for receiving 101B are arranged. The ultrasonic sensor 101 has a concaved surface in the longitudinal direction (Y axis direction) of elements of the transducer element groups (101B$_1$ and 101B$_2$) that form the ultrasonic array sensor for receiving 101B, while the longitudinal direction (Y axis direction) is perpendicular to the normal direction (Z axis direction) of the elements and the X axis direction.

In the example illustrated in FIG. 8, the single element ultrasonic sensor for transmitting 101A and the ultrasonic array sensor for receiving 101B (101B$_1$ and 101B$_2$) are arranged on the saddle type surface TS.

Accordingly, an acoustic field 1302A of an ultrasonic wave transmitted by the single element ultrasonic sensor for transmitting 101A is focused in the Y axis direction and spreads in the X axis direction. An acoustic field 1303C of an ultrasonic wave to be received can be focused in the longitudinal direction (Y axis direction) of the transducer elements, whereas an effect of the focusing in the Y axis direction is not obtained in the image processing. Therefore, a range in which the acoustic field of the ultrasonic wave transmitted intersects with the acoustic field of the ultrasonic wave to be received can be efficiently formed, and an SN ratio of an image can be improved.

The protruding surface portions that extend in the X axis direction are formed for the acoustic field of the ultrasonic wave to be received, and the protruding surface normally makes the acoustic field of the ultrasonic wave to be received spread. However, since the ultrasonic sensor 101 has an array structure, the focusing effect can be obtained in the process of processing a signal in order to form an image, and an effect of spreading the acoustic field of the ultrasonic wave to be received can be offset.

Second Modified Example

Figure 9:
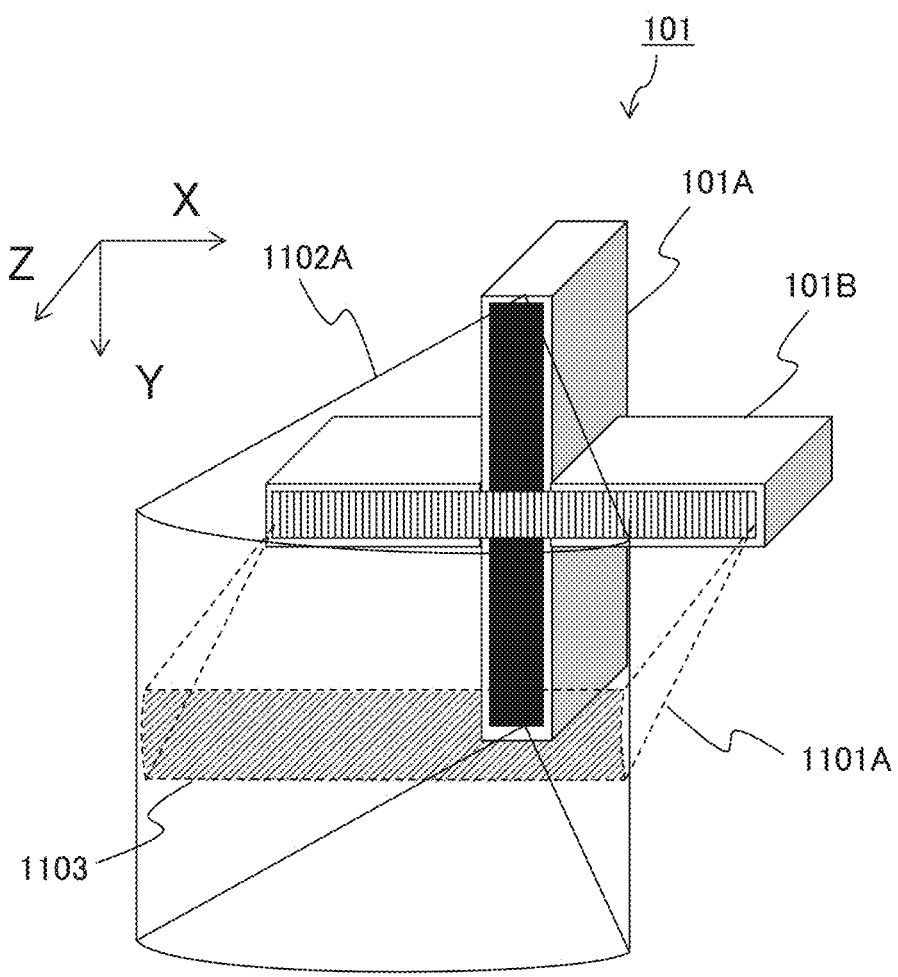
FIG. 9 is a diagram illustrating a configuration of an ultrasonic sensor according to a second modified example.

A configuration of the ultrasonic sensor 101 according to a second modified example will now be described with reference to FIG. 9. FIG. 9 is a diagram illustrating the configuration of the ultrasonic sensor 101 according to the second modified example.

The ultrasonic sensor 101 having transmission and reception integrated in FIG. 9 has the single element ultrasonic sensor for transmitting 101A and the ultrasonic array sensor for receiving 101B that intersect with each other in a cross shape (or extend in the directions perpendicular to each other).

An acoustic field 1101A of an ultrasonic wave to be received by the ultrasonic array sensor for receiving 101B widely spreads in the X axis direction. An acoustic field 1102A of the single element ultrasonic sensor for transmitting 101A spreads in the X axis direction, and a region that can be imaged is represented by reference numeral 1103.

Third Modified Example

Figure 10:
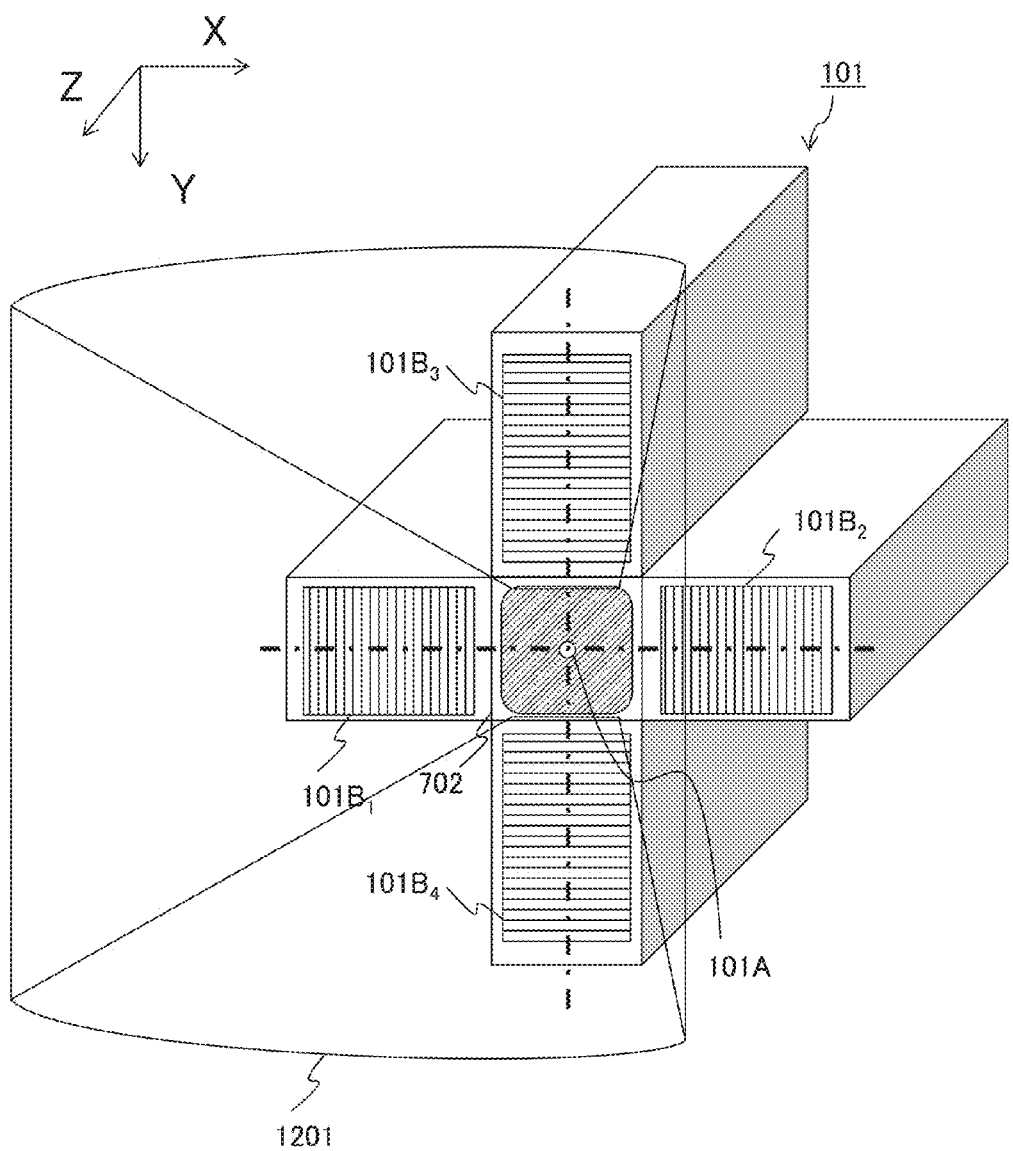
FIG. 10 is a diagram illustrating a configuration of an ultrasonic sensor according to a third modified example.

A configuration of the ultrasonic sensor 101 according to a third modified example will now be described with reference to FIG. 10. FIG. 10 is a diagram illustrating the configuration of the ultrasonic sensor 101 according to the third modified example.

Although the ultrasonic sensor 101 that has the configuration illustrated in FIG. 9 still can image an object to be observed, a region that is included in a region of the acoustic field 1102A of the ultrasonic wave transmitted and used for the formation of the intersecting region 1103 is narrow, which may lead to fear for a low efficiency and a low SN ratio.

As an example of improving the aforementioned case, transducer elements of the ultrasonic sensor 101 are arranged not only in X axis direction but also in Y axis direction as illustrated in FIG. 10, for example. The ultrasonic sensor 101 illustrated in FIG. 10 is configured by the expanded (or transformed) ultrasonic sensor 101 illustrated in FIG. 4.

Groups 101B$_3$ and 101B$_4$ of transducer elements of the ultrasonic sensor 101 are arranged in the Y axis direction or the vertical direction as a part of the ultrasonic array sensor for receiving 101B. Even when an acoustic field 1201 formed by the single element ultrasonic sensor for transmitting 101A is wide, an acoustic field of an ultrasonic wave to be received by the ultrasonic array sensor for receiving 101B in an XY plane can be increased, and a range that enables the ultrasonic imaging to be executed can be expanded.

Second Comparative Example

Figure 11:
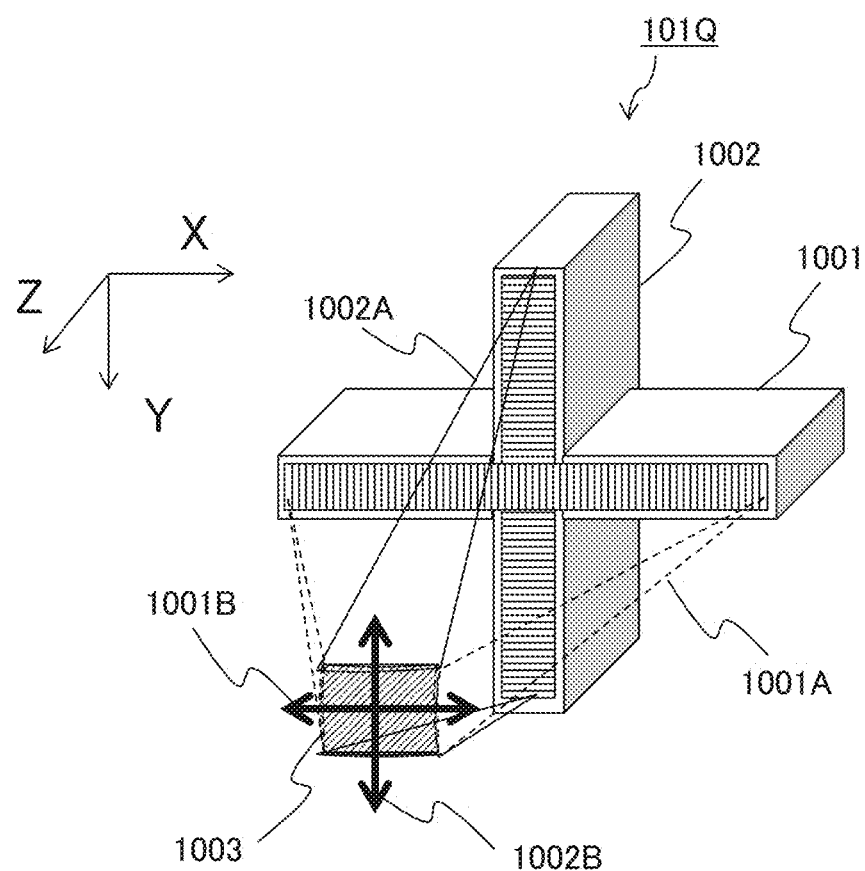
FIG. 11 is a diagram illustrating a configuration of an ultrasonic sensor according to a second comparative example.

A configuration of an ultrasonic sensor 101Q according to a second comparative example will now be described with reference to FIG. 11. FIG. 11 is a diagram illustrating the configuration of the ultrasonic sensor 101Q according to the second comparative example.

A receiving array sensor 1001 forms an acoustic field 1001A of an ultrasonic wave to be received. A transmitting array sensor 1002 forms an acoustic field 1002A of an ultrasonic wave transmitted. Since the transmitting and receiving array sensors 1002 and 1001 each have an array of elements, the ultrasonic sensor 101Q needs to transmit an ultrasonic wave in accordance with delay control of a phased array system or execute electronic scanning in a direction in which an ultrasonic wave is received. Thus, a transceiver cannot be downsized. In addition, a region 1003 in which the acoustic field 1002A intersects with the acoustic field 1001A is small.

Second Embodiment

Figure 12:
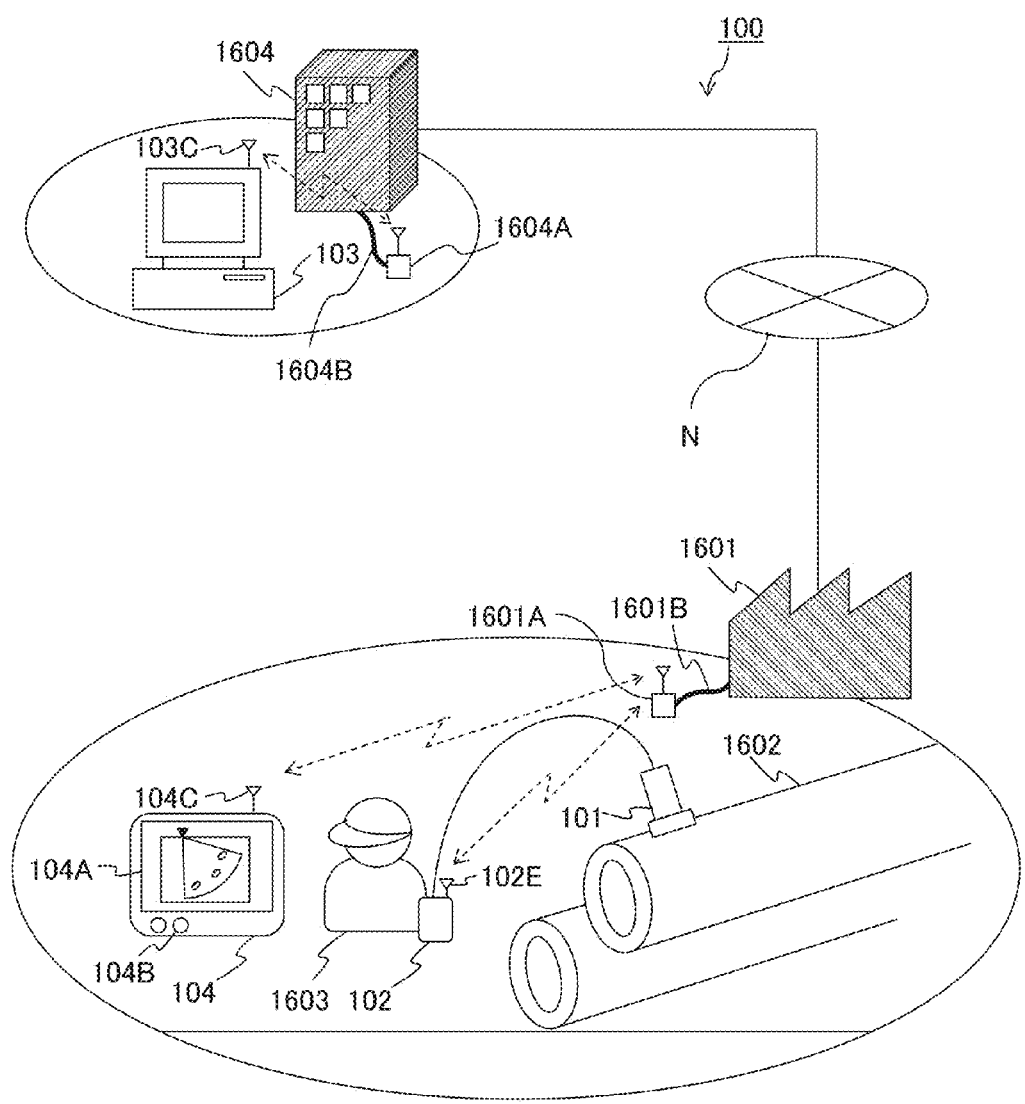
FIG. 12 is a schematic diagram illustrating a configuration of the ultrasonic observation equipment according to a second embodiment of the invention.

A configuration of the ultrasonic observation system 100 that includes the ultrasonic observation equipment 10 according to a second embodiment of the invention will now be described with reference to FIG. 12. FIG. 12 is a diagram illustrating the configuration of the ultrasonic observation system 100 that includes the ultrasonic observation equipment 10 according to the second embodiment of the invention.

Hereinafter, a case in which a plant is inspected will now be described as an example. A cramped portion in which objects 1602 to be inspected that are tubes and the like are arranged close to each other is included in a building 1601. The cramped portion may lower an operability of an operator 1603. According to the second embodiment, the operability can be improved by use of the small ultrasonic observation equipment as described below.

As illustrated in FIG. 12, the operator 1603 carries the small ultrasonic transceiver 102 and the ultrasonic sensor 101 which is in contact with an object 1602 to be inspected such as a tube.

The communication unit 102E of the small ultrasonic transceiver 102 communicates with a communication relay device 1601A of the plant building 1601 that includes the object to be inspected. The communication relay device 1601A is connected to a communication network N through a cable (communication cable) 1601B, but may be wirelessly connected to the communication network N. The communication relay device 1601A is wirelessly connected to the communication unit 102E, but may be connected to the communication unit 102E through the cable 1601B. The devices connected to the communication relay device 1601A belong to a single communication network.

The small ultrasonic transceiver 102 is connected through the relay device 1601A to the processing unit 103 installed in an external office 1604 by way of communication. The processing unit 103 uses the communication unit 103C to communicate with a communication relay device 1604A installed in the external office 1604. The communication relay device 1604A is connected to the communication network N through a cable 1604B, but may be wirelessly connected to the communication network N. In addition, the relay device 1604A is wirelessly connected to the communication unit 103C, but may be connected to the communication unit 103C through the cable 1604B. The devices connected to the communication relay device 1604A belong to another single communication network.

The processing unit 103 generates an ultrasonic image on the basis of signals of a received wave transmitted from the small ultrasonic transceiver 102. The processing unit 103 uses the communication unit 103C to transmit the generated ultrasonic image through the relay device 1604A of the external office 1604, the communication network N, and the relay device 1601A installed in the plant building 1601 to the communication unit 104C of the external display unit 104.

The external display unit 104 displays the ultrasonic image and the user interface 104B on the display unit 104A. The user interface 104B is used for the operator 1603 to control the ultrasonic observation equipment.

The operator 1603 who performs a task of observing the cramped portion included in the plant only needs to take the small ultrasonic transceiver 102 with himself/herself. Since the external display unit 104 is wirelessly connected to the relay device 1601A, the external display unit 104 can be placed at any location as long as the external display unit 104 is connected to the relay device 1601A and does not lower the operability.

As described above, according to the present embodiment, an object to be observed located at a cramped portion can be easily visualized with the use of an ultrasonic wave while the quality of an ultrasonic image is maintained. In addition, a cramped portion can be observed in air by the operator while an image can be displayed at a high speed.

An example of the effects of the first and second embodiments will now be described below. The small ultrasonic transceiver 102 converts received signals into digital signals and transmits the digital signals to a processing system installed in the external office without performing complex delay control, unlike conventional techniques. After the digital signals are subjected to image processing by the processing system, the image data is transmitted again and displayed by the external display unit 104 installed in an external device. In this manner, the transceiver handles only raw data of digital signals without executing delay synthesis and additive synthesis on a received wave. Thus, the equipment can be downsized, and transportation into a cramped portion and observation of the cramped portion can be achieved.

A signal having its received wave going through analog-to-digital conversion (A/D conversion) is subjected to image synthesis by the processing system (processing unit 103) installed in the external office. The processing system is connected to the small transceiver 102 through communication. Thus, the processing system may have a large-capacity memory and a high-accuracy arithmetic element, each of which may be required for high-speed image synthesis. In addition, the processing system is configured as an external device. Even if the volume of the processing system is large, the processing system will not affect the volume of the small ultrasonic transceiver and the volume of the ultrasonic sensor, each of which may be placed near an object to be observed, and the processing system will not reduce operability at the cramped portion.

Ultrasonic image data is displayed on the external display unit 104. The external display unit 104 is a system configured as an external device. Thus, even if the display unit 104A is a monitor with a large display area or the like, the external display unit 104 will not reduce the operability at the cramped portion.

The invention is not limited to the aforementioned embodiments and includes various modified examples. For example, the embodiments are described in detail in order to clearly describe the invention and are not limited to the system and the equipment that have the configurations described above. A part of a configuration described in the first or second embodiment may be replaced with a part of a configuration described in the other embodiment. A part of a configuration described in the first or second embodiment may be added to a configuration described in the other embodiment. A part of the configurations described in the first and second embodiments may be deleted.

For example, in the second embodiment, the communication network to which the devices connected to the communication relay device 1601A belong is directly connected to the communication network to which the devices connected to the communication relay device 1604A belong without the communication network N.

What is claimed is:

1. An ultrasonic observation equipment comprising:
   an ultrasonic sensor including:
      a single element ultrasonic sensor including a single transducer element and configured to transmit an ultrasonic wave to an inspection target on a basis of a pulse wave; and
      an ultrasonic array sensor, different from the single element ultrasonic sensor, including a plurality of transducer elements and configured to receive an ultrasonic reflected wave reflected from the inspection target;
   an ultrasonic transceiver unit including:
      a pulsar configured to supply the pulse wave to the single element ultrasonic sensor;
      a receiver configured to receive an electric signal from the transducer elements included in the ultrasonic array sensor;
      an amplification and conversion unit configured to amplify the electric signal of each of the transducer elements included in the ultrasonic array sensor received by the receiver, convert the electric signal into a digital signal, and arrange the digital signal in a serial order so as to generate a serial digital signal; and
      a first communication unit configured to transmit the serial digital signal;
   a processing unit comprising:
      a second communication unit configured to receive the serial digital signal, and
      an image generator configured to generate an image on a basis of the serial digital signal; and
   a third communication unit configured to transmit and receive data between the ultrasonic transceiver unit and the processing unit;
   wherein the serial digital signal is transmitted from the ultrasonic transceiver unit to the third communication unit via a single cable.

2. The ultrasonic observation equipment according to claim 1,
   wherein the single element ultrasonic sensor and the ultrasonic array sensor are arranged in such a manner that a center of the single element ultrasonic sensor matches a center of the ultrasonic array sensor.

3. The ultrasonic observation equipment according to claim 2,
   wherein the ultrasonic array sensor includes a first transducer element group and a second transducer element group, and
   wherein the single element ultrasonic sensor is arranged between the first transducer element group and the second transducer element group.

4. The ultrasonic observation equipment according to claim 3,
   wherein the single element ultrasonic sensor and the ultrasonic array sensor are arranged on a saddle type surface.

5. The ultrasonic observation equipment according to claim 3,
wherein the ultrasonic array sensor includes a third transducer element group and a fourth transducer element group, and
wherein the single element ultrasonic sensor is arranged between the third transducer element group and the fourth transducer element group.

6. The ultrasonic observation equipment according to claim 2,
wherein the single element ultrasonic sensor and the ultrasonic array sensor are arranged in such a manner as to be perpendicular to each other.

7. An ultrasonic observation system comprising:
a single element ultrasonic sensor including a single transducer element and configured to transmit an ultrasonic wave on a basis of a pulse wave;
an ultrasonic array sensor, different from the single element ultrasonic sensor, including a plurality of transducer elements and configured to receive an ultrasonic reflected wave;
a transducer including: a pulsar configured to supply the pulse wave to the single element ultrasonic sensor; a receiver configured to receive an electric signal from the transducer elements included in the ultrasonic array sensor; and an amplification and conversion unit configured to amplify the electric signal of each of the transducer elements included in the ultrasonic array sensor received by the receiver, convert the electric signal into a digital signal, and arrange the digital signal in a serial order so as to generate a serial digital signal;
a processing unit including an image generator configured to generate an image on a basis of the serial digital signal;
a relay unit configured to transmit and receive data between the transducer and the processing unit; and
a display unit configured to display the image,
wherein the single element ultrasonic sensor, the ultrasonic array sensor, the transceiver, and the display unit are connected to a first communication network,
wherein the processing unit is connected to a second communication network,
wherein the first communication network is connected to the second communication network, and
wherein the serial digital signal is transmitted from the transducer to the processing unit via a single cable.

8. An ultrasonic observation method comprising:
supplying a pulse wave to a single element ultrasonic sensor;
causing the single element ultrasonic sensor including a single transducer element to transmit an ultrasonic wave on a basis of the pulse wave;
causing an ultrasonic array sensor, different from the single element ultrasonic sensor, including a plurality of transducer elements to receive an ultrasonic reflected wave;
receiving, by an ultrasonic transceiver unit, an electric signal from the transducer elements included in the ultrasonic array sensor;
amplifying the electric signal of each of the transducer elements included in the ultrasonic array sensor, converting the electric signal into a digital signal, and arranging the digital signal in a serial order so as to generate a serial digital signal; and
transmitting the serial digital signal from the ultrasonic transceiver unit to a processing unit including an image generator via a single cable; and
generating, by the image generator, an image based on the serial digital signal.

9. The ultrasonic observation equipment according to claim 1, further comprising:
a serial cable connecting the ultrasonic transceiver unit with the processing unit via the third communication unit.

* * * * *